United States Patent

Kitamura et al.

[11] B 4,013,639

[45] Mar. 22, 1977

[54] PREPARATION OF ASYMMETRIC IMINODIBENZYL COMPOUNDS

[75] Inventors: Ryoichi Kitamura; Eiichi Kitamura; Tetsuo Kitamura; Tameo Kitamura, all of Suita, Japan

[73] Assignees: Eiichi Kitamura; Tetsuo Kitamura; Tameo Kitamura, all of Osaka, Japan

[22] Filed: July 24, 1973

[21] Appl. No.: 382,120

[44] Published under the second Trial Voluntary Protest Program on March 23, 1976 as document No. B 382,120.

[30] Foreign Application Priority Data

July 24, 1972 Japan .............................. 47-74367
July 24, 1972 Japan .............................. 47-74368

[52] U.S. Cl. .......................... 260/239 D; 260/571; 260/578; 260/580; 260/612 R; 260/645; 260/646; 260/954

[51] Int. Cl.² .................................... C07D 223/28

[58] Field of Search ................. 260/239 D

[56] References Cited

UNITED STATES PATENTS 2,764,580   9/1956   Schindler et al. ............. 260/239 D
3,068,222  12/1962   Craig ............................. 260/239 D

OTHER PUBLICATIONS

Horner et al., Ber. Deut. Chem., vol. 91, pp. 61–63, (1958).

Seus et al., J. Org. Chem., vol. 26, p. 5243 (1961).

*Primary Examiner*—Alton D. Rollins
*Attorney, Agent, or Firm*—Birch, Stewart, Kolasch and Birch

[57] ABSTRACT

Iminodibenzyl derivatives of the formula:

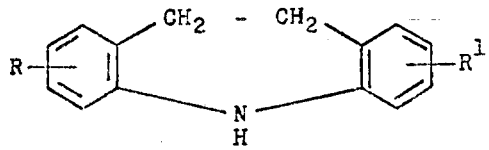

wherein R and $R^1$ each represent hydrogen, halogen, amino, sulfamoyl, lower alkyl, lower alkoxy or lower alkanoyl, provided that R and $R^1$ can not both be hydrogen and when R and $R^1$ are the same, they are located at positions asymmetric to each other, are produced in high purity and yield by a series of reactions which proceed through novel 2,2'-dinitrostilbene or 2,2'-diaminostilbene and 2,2'-diaminodibenzyl derivatives. The reaction sequence involves condensation, reduction and ring-closure reactions to give asymmetric as well as symmetric iminodibenzyl derivatives. The resulting iminodibenzyl derivatives may be converted to useful pharmaceutical compounds having antidepressant, analgesic or anti-allergic properties.

8 Claims, No Drawings

PREPARATION OF ASYMMETRIC IMINODIBENZYL COMPOUNDS

The present invention relates to iminodibenzyl derivatives, their intermediates, and processes for producing them. More particularly, the present invention relates to 10,11-dihydro-5H-dibenz[b,f]azepines, intermediates useful for preparing the same, and processes for the production of the 10,11-dihydro-5H-dibenz[b,f]azepines and their intermediates. The 10,11-dihydro-5H-dibenz[b,f]azepines of the present invention are themselves useful as intermediates for the preparation of, for example, N-dialkylaminoalkyl-3-chloroiminodibenzyl compounds, such as 5-(gamma-dimethylaminopropyl)-3-chloroiminodibenzyl, which is effective as having anti-depressant, analgesic, and anti-allergic properties.

There has been a strong demand to industrially manufacture 10,11-dihydro-5H-dibenz[b,f]azepines which may be converted to, for example, N-dialkylaminoalkyl-3-chloroiminodibenzyl compounds or 5-dialkylaminoalkyl-3-chloro-10,11-dihydro-5H-dibenz[b,f]azepines. Heretofore, methods and processes for preparing, in particular, asymmetric iminodibenzyl derivatives have been reported in a relatively small number of publications. The known processes for preparing the asymmetric iminodibenzyl derivatives are; for example, reduction of 3-chloroiminostilbene (*Journal of Organic Chemistry*, 26, 135 (1961)), elimination of one chlorine atom from 3,7-dichloroiminodibenzyl by reduction with hydrogen (U.S. Pat. No. 3,056,776) and replacement of the diazonium group by a chlorine atom in 5-acetyl-3-aminoiminodibenzyl previously diazotized by means of the Sandmeyer reaction (U.S. Pat. No. 3,056,774). These known processes require the use of expensive reagents, which make these processes unsuited for the commercial manufacture of the asymmetric iminodibenzyl derivatives. Moreover, these processes involve a selective introduction of a substituent into either of the two benzene rings or a selective elimination of either of two substituents on the benzene rings, thereby necessarily resulting in the by-production of the symmetric iminodibenzyl derivatives. This by-production will sometimes cause disadvantages in manufacturing the asymmetric iminodibenzyl derivatives.

Accordingly, it is an object of the present invention to provide a process which is particularly suited for producing asymmetric iminodibenzyl derivatives.

Another object of the present invention is to provide novel intermediates useful for preparing said asymmetric iminodibenzyl derivatives.

A further object of the present invention is to provide a process for producing said intermediates.

A further object of the present invention is to provide a process for producing symmetric as well as asymmetric intermediates which are both useful as intermediates for drugs.

Other objects, features and advantages of the present invention will become apparent during the course of the following description and claims.

As the result of extensive studies, it has been found that an asymmetric iminodibenzyl derivative can be produced in sufficiently high purity and yield through procedures difficult from those heretofore applied by using starting materials less expensive than those used in the prior art processes. A sequence of these procedures can also be used to produce the symmetric iminodibenzyl derivatives. However, these processes have the particular advantage of providing a method for the production of the asymmetric iminodibenzyl derivatives on an industrial scale.

The following reaction sequence, illustrative of the present invention, indicates the series of steps that are used to attain the above objects. Only substituents present at the 1- and 2-positions of the benzene rings are shown herein, it being understood that non-interfering groups may be present at the other positions thereof.

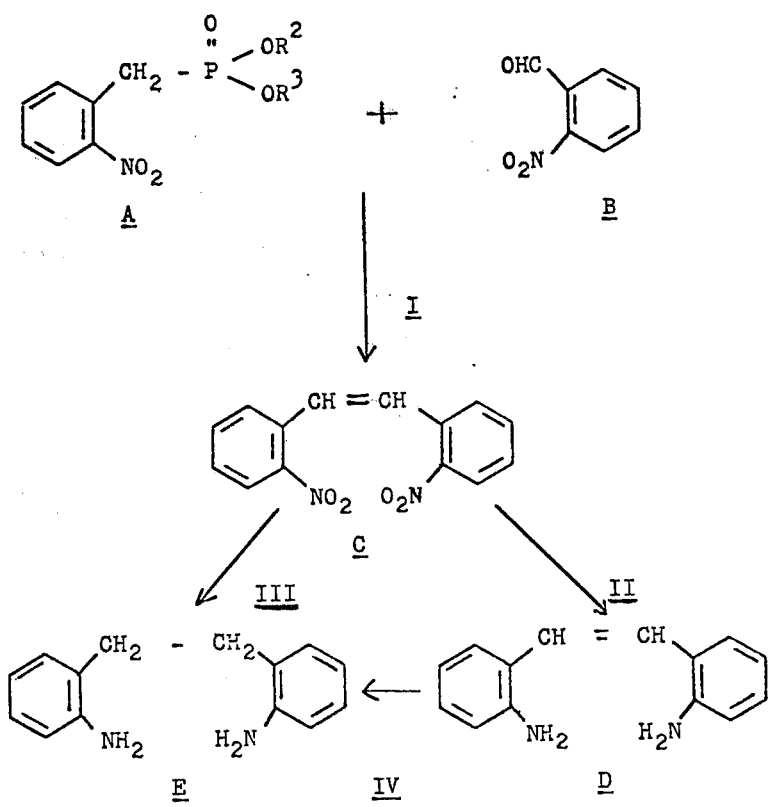

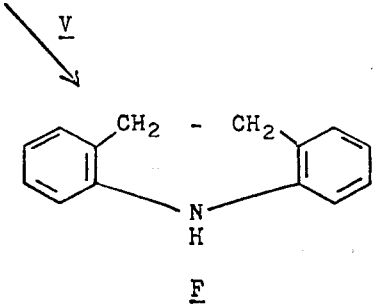

V

F wherein $R^2$ and $R^3$ each represent hydrogen, lower alkyl, aryl or aryl-lower alkyl, provided that when one of $R^2$ and $R^3$ is hydrogen, the other is not hydrogen. The lower alkyl radical may include alkyl groups having from 1 to 6 carbon atoms such as methyl, ethyl, propyl, and the like; the aryl radical may include phenyl, lower alkyl-substituted phenyl such as tolyl, and the like; and the aryl-lower alkyl (aralkyl) radical may include benzyl, phenylethyl, and the like.

Among the compounds as shown above, the intermediates C, D, and E are all useful for the preparation of the other intermediates F, which may be further converted to valuable medicines. More particularly, 2,2'-dinitrostilbene C, 2,2'-diaminostilbene D, and 2,2'-diaminodibenzyl E are all novel and, for purposes of simplifying further explanations about these compounds, they may be respectively illustrated as follows:

radical includes acetyl, propionyl, and the like. However, since any other substituents that are known and obvious to persons skilled in the art to be substantially inert during the course of the reactions and which cause no adverse pharmacological effect may be used for purposes of the present invention, R and $R^1$ should not be construed to be limited merely to those illustrated above.

It is to be noted that since the steps I, II, III and IV are applicable to the production of the symmetric intermediates C, D, and E as well as the novel asymmetric intermediates, R and $R^1$ are interchangeable, but when it is desired to obtain the novel intermediates, the substituents R and $R^1$ should be asymmetrically attached to the respective positions of the benzene rings.

Another feature and embodiment of the present invention involves a ring-closure of the 2,2'-diaminodi-

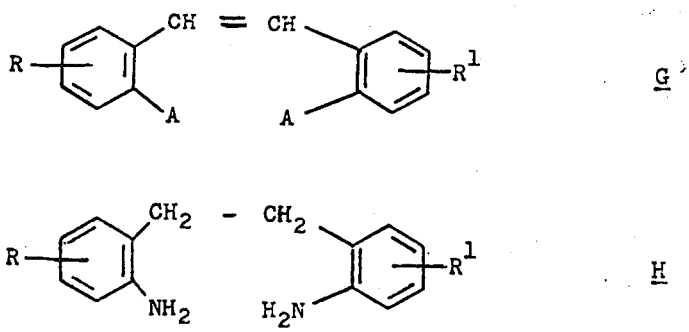

G and

H wherein A is nitro or amino and R and $R^1$ each represent one or more substituents selected from the group consisting of hydrogen, halogen, sulfamoyl, amino, lower alkyl, lower alkoxy and lower alkanoyl, and R and $R^1$ is specifically different when their substituents are at positions symmetric to each other; moreover, when one of R and $R^1$ is hydrogen, the other is not hydrogen.

The said halogen atom includes chlorine, bromine, iodine, and the like. The lower alkyl radical per se and as a part of other substituents includes a monovalent straight or branched-chain hydrocarbon residue of 1 to 6 carbon atoms such as methyl, ethyl, propyl, butyl, and the like. The lower alkoxy radical includes oxygen-containing lower alkyl of 1 to 6 carbon atoms such as methoxy, ethoxy, and the like. The lower alkanoyl benzyl compounds H to give an iminodibenzyl derivative of the following general formula:

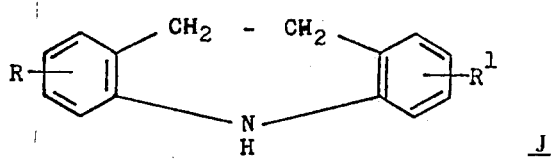

J wherein R and $R^1$ are as defined above.

In accordance with the present invention, the step I involves a condensation reaction between a 2-nitrobenzyl phosphonic ester A and a 2-nitrobenzaldehyde B. The condensation may usually be effected at room or at reflux temperatures in an inert organic solvent in the presence of a condensing agent. The organic solvent may include a polar solvent such as an alkanol, for example, methanol, ethanol, and the like. The condensing agent may be an alkali metal alcoholate such as, for example, sodium methylate, sodium ethylate, potassium ethylate, and lithium ethylate, sodium hydride, sodium amide, and the like.

The procedures which follow the step I involve a reduction reaction of a 2,2'-dinitrostilbene compound C to a 2,2'-diaminodibenzyl compound E. The 2,2'-dinitrostilbene compound C may be reduced by a one-step process III or by two-step processes II + IV. The 2,2'-dinitrostilbene compound C may be contact-reduced to the 2,2'-diaminodibenzyl compound E by using hydrogen in the presence of a catalyst such as Raney nickel, platinum oxide, and palladium on a carrier (e.g. carbon, barium sulfate). Alternatively, the 2,2'-dinitrostilbene compound C may be reduced to the 2,2'-diaminodibenzyl compound E by treatment with a reducing agent such as metallic sodium and amyl alcohol. The two-step process involves, first, a reduction reaction of the 2,2'-dinitrostilbene C and, secondly, a contact reduction of the 2,2'-diaminostilbene D. The first reduction may be carried out by using a reducing agent, such as stannous chloride, iron and hydrochloric acid, or zinc and hydrochloric acid. The second contact reduction reaction may be effected with hydrogen in the presence of a catalyst such as Raney nickel, platinum oxide, palladium on a carrier (e.g. carbon, barium sulfate), and the like. In the alternative, the reduction in the second stage may be accomplished by treatment with a reducing agent such as metallic sodium and amyl alcohol.

The step V involves a ring-closure of the 2,2'-diaminodibenzyl compound E, forming the iminodibenzyl derivative F. The step V is preferably applied to the preparation of the asymmetric iminodibenzyl derivatives J from the asymmetric 2,2'-diaminodibenzyl H. However, this ring-closure reaction may also be used to form the symmetric iminodibenzyl derivatives in substantially the same manner as with the asymmetric 2,2'-diaminodibenzyl derivatives. The ring-closure reaction may be conducted in a variety of processes. When the 2,2'-diaminodibenzyl compound is in its free form the ring-closure may be accomplished by heating it in the presence of a catalyst. Such catalyst may be selected from metallic salts, ammonium salts, phosphorus halides, phosphorus oxyhalides, complex compounds thereof with 2,2'-diaminodibenzyls, hydrohalides of 2,2'-diaminodibenzyls, iodine, ammonium complexes of metals and the like. When the 2,2'-diaminodibenzyl compound is in the form of a salt, such as a phosphate, hydrochloride, a lower alkyl-sulfonate, a phenylsulfonate, a phenyl lower alkylsulfonate, and the like, the 2,2'-diaminodibenzyl compound may be ring-closed by the mere application of heat. The 2,2'-diaminodibenzyl compound in its free form may also be ring-closed by heating it together with the 2,2'-diaminodibenzyl compound in the salt form or with polyphosphoric acid. Although the temperature of heating is usually from about 200° C. to 400° C., the ring-closure reaction may be readily effected at relatively low temperatures when the free 2,2'-diaminodibenzyl is used in the presence of a catalyst or with its salt compound.

The iminodibenzyl derivatives J of the present invention may be converted by introducing a dialkylaminoalkyl radical or a similar pharmacologically nontoxic group into the nitrogen atom at the 5-position in a conventional manner to give compounds useful as antidepressants, analgesics, and/or anti-allergic agents.

The following examples are given merely as illustrative of the present invention, and they are not to be considered as limiting.

EXAMPLE 1

A. In a solution of 0.68 g. of sodium ethylate in 20 ml. of ethanol, 2.7 g. of diethyl ortho-nitrobenzyl phosphonate was dissolved. To this solution was dropwise added a solution of 1.5 g. of ortho-nitrobenzaldehyde in 20 ml. of ethanol with stirring at ambient temperature. After the stirring was continued for 30 min., the crystals formed were filtered and washed with a small amount of ethanol to give 2.3 g. (85.2% yield) of trans-2,2'-dinitrostilbene. The product which had been recrystallized from chloroform had a melting point of 195° to 196° C.

B. A solution of 2.7 g. of trans-2,2'-dinitrostilbene in 40 ml. of tetrahydrofuran was stirred for 15 hours at 15° C. while using Raney nickel as a catalyst and introducing hydrogen gas at atmospheric pressure into the solution. After the absorption of hydrogen gas was terminated, the catalyst was filtered off, and the solvent was distilled off to leave crystalline materials which were in turn recrystallized from a benzene-petroleum ether mixture to give 1.85 g. (87% yield) of 2,2'-diaminodibenzyl melting at 75° to 76° C.

EXAMPLE 2

A. In a solution of 1.6 g. of sodium methylate in 20 ml. of methanol, 8.2 g. of diethyl ortho-nitrobenzyl phosphonate was dissolved. To this solution was dropwise added a solution of 5.5 g. of 2-nitro-4-chlorobenzaldehyde in 20 ml. of methanol with stirring at ambient temperature. After stirring continuously for one hour, crystalline materials formed which were filtered and washed with a small amount of ethanol and water to give 8.2 g. (90% yield) of trans-2,2'-dinitro-4-chlorostilbene. Recrystallization of this compound from ethyl acetate gave a product having a melting point of 158.5° to 159° C.

B. To 70 ml. of glacial acetic acid was added 27 g. of anhydrous stannous chloride, and then dry hydrogen chloride gas was blown into the mixture to dissolve the stannous chloride. While stirring the solution, 4 g. of trans-2,2'-dinitro-4-chlorostilbene was gradually added while maintaining the temperature of the solution at 25° to 30° C. After the solution was left overnight, the stannous complex salt formed was filtered and then washed with a small amount of glacial acetic acid. The complex salt was decomposed by adding 120 ml. of a 20% solution of sodium hydroxide thereto and then extracted with ethyl acetate. Then, the solvent was distilled off, thereby leaving a residue to which a small amount of benzene was added. After the solution was left standing for a while, there were formed 2.65 g. (82.5% yield) of pale yellow crystals of trans-2,2'-diamino-4-chlorostilbene. The product, after being recrystallized from benzene, had a melting point of 117.5° to 118° C.

C. A solution of 12.2 g. of trans-2,2'-diamino-4-chlorostilbene in 80 ml. of tetrahydrofuran was shaken for 15 hours at 15° C. with Raney nickel as a catalyst while introducing hydrogen gas under atmospheric pressure. After the absorption of hydrogen was terminated, filtering off of the catalyst, followed by the removal of the solvent, afforded crystals which were then recrystallized from isopropanol to give 10.9 g. (88.6% yield) of 2,2'-diamino-4-chlorodibenzyl. The product was further vacuum distilled to provide a fraction having a boiling point of 176° to 183° C. at 0.4 mmHg which was in turn recrystallized from isopropanol to give a product melting at 97.5° to 98° C.

D. A mixture of 3 g. of 2,2'-diamino-4-chlorodibenzyl and 0.1 g. of anhydrous aluminum chloride was heated at 290° to 315° C. for 50 minutes with stirring. The cooled reaction mixture was extracted a few times with benzene. The undissolved materials were filtered off, and the unreacted 2,2'-diamino-4-chlorodibenzyl dihydrochloride formed by adding dilute hydrochloric acid and shaking was recovered in the amount of 1.11 g. The filtrate was separated, and the benzene layer was washed with water and dried over anhydrous potassium carbonate. Removal of the solvent gave 1.39 g. (70% yield) of 3-chloroiminodibenzyl which was then vacuum distilled. A fraction having a boiling point of 145° to 150° C. at 0.3 mmHg was collected and then recrystallized from a benzene-petroleum ether mixture to give 3-chloroiminodibenzyl melting at 87.5° to 88° C.

EXAMPLE 3

A. To a solution of 16.5 g. of 2-nitro-4-chlorobenzyl alcohol in 200 ml. of chloroform was added dropwise 13 g. of phosphorus tribromide, and the mixture was heated to reflux for 1 hour on a water bath. The reaction mixture was then poured into water, and the chloroform layer was separated and washed with water. After the solvent was removed, the residue was extracted with ligroin while warming and allowed to stand to form colorless acicular crystals of 2-nitro-4-chlorobenzyl bromide (80% yield) melting at 42° to 43° C.

A solution of 6.3 g. of 2-nitro-4-chlorobenzyl bromide and 4.2 g. of triethyl phosphite in 5 ml. of toluene was heated to 110° C. for 1 hour on an oil bath with stirring, and the ethyl bromide formed was removed therefrom. After the reaction was completed, the reaction mixture was condensed under reduced pressure on a water bath to give 8 g. of crude diethyl 2-nitro-4-chlorobenzyl phosphonate which was then dissolved in a solution of 0.9 g. of sodium metal in 50 ml. of alcohol. To the solution was dropwise added a solution of 3.8 g. of ortho-nitrobenzaldehyde in 50 ml. of ethanol with stirring at ambient temperature. After being stirred for 1 hour, the solution was filtered to give crystalline materials which were then washed with a small amount of ethanol to give 6.0 g. of trans-2,2'-dinitro-4-chlorostilbene. Its yield with respect to 2-nitro-4-chlorobenzyl bromide was 78.9%. It was recrystallized from ethyl acetate to give a product melting at 158.5° to 159° C.

B. A solution of 10 g. of trans-2,2'-dinitro-4-chlorostilbene in 100 ml. of tetrahydrofuran was contact reduced using Raney nickel as a catalyst in substantially the same manner as in Example 2(C). It was found that 107% of hydrogen with respect to that theoretically calculated was absorbed. The crystalline materials formed were recrystallized from isopropanol to give 7.2 g. (88.9% yield) of 2,2'-diamino-4-chlorodibenzyl melting at 97° to 98° C.

C. A mixture of 3 g. of 2,2'-diamino-4-chlorodibenzyl and 0.1 g. of ammonium bromide was heated at 310° to 335° C. for 2.5 hours and treated by the method of Example 2(D) to give 1.27 g. of 3-chloroiminodibenzyl. The amount of the unreacted amine dihydrochloride recovered was 1.3 g.

EXAMPLE 4

A. To a solution of 1.4 g. of sodium methylate in 40 ml. of ethanol was added 6.8 g. of diethyl ortho-nitrobenzyl phosphonate. While stirring the solution at ambient temperature, a solution of 4.1 g. of 2-nitro-4-methylbenzaldehyde in 40 ml. of ethanol was dropwise added. After being stirred for 1.5 hours and allowed to stand overnight, the yellow crystals formed were filtered and washed with a small amount of ethanol to give 6.0 g. (85% yield) of trans-2,2'-dinitro-4-methylstilbene. This compound was then recrystallized from benzene to give a product melting at 170° to 171° C.

B. A solution of 2 g. of trans-2,2'-dinitro-4-methylstilbene in 50 ml. of tetrahydrofuran was subjected to a contact reduction using Raney nickel as a catalyst in substantially the same manner as in Example 1(B) to give a crystalline material which was then recrystallized from a benzene - petroleum benzin mixture. The product obtained was 1.4 g. (87.5% yield) of colorless rhombohedral crystals of 2,2'-diamino-4-methyldibenzyl melting at 78.5° to 79° C.

EXAMPLE 5

A. Using 4.5 g. of 2-nitro-4-methoxybenzaldehyde as a starting material, substantially the same reaction as in Example 4(A) was carried out to give 6.2 g. (82.6% yield) of trans-2,2'-dinitro-4-methoxystilbene. Recrystallization thereof from benzene gave a product having a melting point of 142° to 143° C.

B. A solution of 2 g. of trans-2,2'-dinitro-4-methoxystilbene in 50 ml. of tetrahydrofuran was contact-reduced using Raney nickel as a catalyst by the procedure of Example 1(B) and then vacuum distilled to give a fraction having a boiling point of 182° to 188° C. at 0.4 mmHg which yielded 1.51 g. (93.6% yield) of 2,2'-diamino-4-methoxydibenzyl. It was recrystallized from benzene to give a product having a melting point of 89.7° to 90° C.

EXAMPLE 6

A. In a solution of 1 g. of metallic lithium in 150 ml. of ethanol, 27.5 g. of diethyl ortho-nitrobenzyl phosphonate was dissolved. While stirring the solution at ambient temperature, a solution of 18.11 g. of 2-nitro-4-methoxybenzaldehyde in 300 ml. of ethanol was dropwise added. After being stirred for 1.5 hours while cooling with water and allowed to stand overnight, the yellow crystals formed were filtered and washed with a small amount of ethanol to give 25.5 g. (85% yield) of trans-2,2'-dinitro-4-methoxystilbene.

B. Using trans-2,2'-dinitro-4-methoxystilbene as a starting material, a contact reduction reaction was effected by the method of Example 1(B) to give 2,2'-diamino-4-methoxydibenzyl.

EXAMPLE 7

A. In a solution of 1.1 g. of sodium methylate in 32 ml. of ethanol, 6.2 g. of diethyl 2-nitro-4-chlorobenzyl phosphonate was dissolved. A solution of 3.7 g. of 2-nitro-4-chlorobenzaldehyde in 32 ml. of ethanol was dropwise added to said solution with stirring at ambient temperature. After the solution was stirred for 1 hour, the yellow crystalline materials formed were filtered and washed with a small amount of ethanol to give 5 g. (74% yield) of trans-2,2'-dinitro-4,4'-dichlorostilbene. Its recrystallization from glacial acetic acid gave a product having a melting point of 247° to 248° C.

B. Using 2 g. of trans-2,2'-dinitro-4,4'-dichlorostilbene as a starting material, a contact reduction reaction was effected by the method of Example 1(B). A fraction having a boiling point of 205° to 207° C. at 0.55 mmHg was recrystallized from isopropanol to give 1.3 g. (78.4% yield) of 2,2'-diamino-4,4'-dichlorodibenzyl melting at 139.5° to 141° C.

EXAMPLE 8

A. In a solution of 1.2 g. of metallic sodium in 70 ml. of ethanol, 13.5 g. of diethyl 2-nitro-4-chlorobenzyl phosphonate was dissolved. While stirring the solution at ambient temperature, a solution of 7 g. of 2-nitro-4-methylbenzaldehyde in 50 ml. of ethanol was dropwise added. After being stirred below 30° C. for 2 hours and allowed to stand overnight, the yellow crystals formed were filtered to give 9.8 g. (72.5% yield) of trans-2,2'-dinitro-4-chloro-4'-methylstilbene melting at 230° to 230.5° C. (recrystallized from benzene).

B. Using 7 g. of trans-2,2'-dinitro-4-chloro-4'-methylstilbene as a starting material, a contact reduction reaction was effected by the method of Example 1(B). The product was recrystallized from isopropanol to give 4.5 g. (78.6% yield) of 2,2'-diamino-4-chloro-4'-methyldibenzyl as colorless needles melting at 83.5° to 84° C.

EXAMPLE 9

A. In a solution of 2.8 g. of metallic sodium in 150 ml. of ethanol, 32.5 g. of diethyl 2-nitro-4-chlorobenzyl phosphonate was dissolved. While stirring the solution at ambient temperature, a solution of 18.14 g. of 2-nitro-4-methoxybenzaldehyde in 300 ml. of ethanol was dropwise added. After being stirred for 2 hours while cooling with water and allowed to stand overnight, the yellow crystals formed were filtered to give 25.2 g. (75.3% yield) of trans-2,2'-dinitro-4-chloro-4'-methoxystilbene melting at 202° to 202.5° C. (recrystallized from ethyl acetate).

B. Using trans-2,2'-dinitro-4-chloro-4'-methoxystilbene as a starting material, a contact reduction was effected by the method of Example 1(B) to give 2,2'-diamino-4-chloro-4'-methoxydibenzyl.

EXAMPLE 10

To 3 g. of 2,2'-diamino-4-chlorodibenzyl, 0.12 g. of ammonium iodide was added, and the mixture was heated at 300° to 315° C. for 3 hours and treated by the method of Example 2(D) to give 0.95 g. of 3-chloroiminodibenzyl. The amount of the amine dihydrochloride recovered was 1.14 g.

EXAMPLE 11

A mixture of 3 g. of 2,2'-diamino-4-chlorodibenzyl and 0.1 g. of anhydrous ferric chloride was heated at 295° to 315° C. for 1 hour and 20 minutes and treated by the procedure of Example 2(D) to give 1.32 g. of 3-chloroiminodibenzyl. The amount of the amine dihydrochloride recovered was 1.23 g.

EXAMPLE 12

A mixture of 3 g. of 2,2'-diamino-4-chlorodibenzyl and 0.1 g. of cupric bromide was heated at 300° to 320° C. for 2 hours and treated in the manner of Example 2(D) to give 1.25 g. of 3-chloroiminodibenzyl. The amine dihydrochloride was recovered in an amount of 1.1 g.

EXAMPLE 13

A mixture of 3 g. of 2,2'-diamino-4-chlorodibenzyl and 0.1 g. of phosphorus tribromide was heated at 300° to 320° C. for 2.5 hours and treated by the method of Example 2(D) to give 1.3 g. of 3-chloroiminodibenzyl. The amount of the amine dihydrochloride recovered was 0.8 g.

EXAMPLE 14

A mixture of 3 g. of 2,2'-diamino-4-chlorodibenzyl and 0.21 g. of 2,2'-diamino-4-chlorodibenzyl dihydrobromide was heated at 300° to 325° C. for 1 hour and 40 minutes and treated by the procedure of Example 2(D) to give 1.25 g. of 3-chloroiminodibenzyl. The amount of the amine dihydrochloride recovered was 1.67 g.

EXAMPLE 15

A mixture of 1.8 g. of 2,2'-diamino-4-chlorodibenzyl and 1.8 g. of 2,2'-diamino-4-chlorodibenzyl dihydrochloride (melting at 278° C.) was heated at 270° to 280° C. for 4 hours on an oil bath. After the reaction mixture was cooled, it was extracted several times with benzene, and the unreacted amine hydrochloride was filtered. The benzene layer was stirred with dilute hydrochloric acid and the amine hydrochloride formed was then filtered. The combined amount of the recovered amine hydrochloride was 2.1 g. The benzene extract was washed with water, and distillation of the solvent gave 0.84 g. of 3-chloroiminodibenzyl.

EXAMPLE 16

To a solution of 6 g. of 2,2'-diamino-4-chlorodibenzyl in 50 ml. of dioxane or tetrahydrofuran was added dropwise 6.5 g. of 89% phosphoric acid. After being stirred well, the solution was filtered by suction to give the phosphate which formed as a crystalline material which was then washed with ethyl acetate and dried at 105° C. to give 10.3 g. of 2,2'-diamino-4-chlorodibenzyl diphosphate having a melting point of 260° to 263° C. To 8g. of this phosphate was added 24 g. of polyphosphoric acid (nearly corresponding to $H_6P_4O_{13}$). The mixture was heated and stirred at 278° to 282° C. for 40 minutes. The reaction mixture was poured into 150 ml. of ice water and extracted several times with warm benzene. The benzene layer was washed with dilute hydrochloric acid and then with water and dried over anhydrous potassium carbonate. Removal of the solvent left a residue to which a small amount of petroleum benzin was then added to form a crystalline material. Filtration of the solution gave 3.85 g. of 3-chloroiminodibenzyl having a melting point of 78° to 83° C.

EXAMPLE 17

A dropwise addition of 1.0 g. of methyl sulfonic acid was made to 2.47 g. of hot 2,2'-diamino-4-chlorodibenzyl, and the mixture was continuously heated at 295° to 305° C. for 1.5 hours while stirring. The reaction mixture was poured into 30 ml. of ice water to avoid the formation of a viscous mass and extracted several times with benzene. The extract was treated by the method of Example 2(D) to give 0.8 g. of 3-chloroiminodibenzyl having a melting point of 79° to 84° C.

EXAMPLE 18

A mixture of 2.47 g. of 2,2'-diamino-4-chlorodibenzyl and 1.8 g. of para-toluene sulfonate monohydrate was heated at 260° to 285° C. for 40 minutes. After the reaction mixture was cooled, it was crushed, heated to reflux with 40 ml. of benzene and then extracted. The extract was treated by the procedure of Example 2(D) to give 0.45 g. of 3-chloroiminodibenzyl.

EXAMPLE 19

A. In a solution of 1.4 g. of sodium methylate in 40 ml. of ethanol, 6.8 g. of diethyl ortho-nitrobenzyl phosphonate was dissolved. While stirring the solution at ambient temperature, a solution of 4.1 g. of 2-nitro-4-methylbenzaldehyde in 40 ml. of ethanol was dropwise added. After being stirred for 1.5 hours and allowed to stand overnight, the yellow crystals formed were filtered and washed with a small amount of ethanol to give 6.0 g. (85% yield) of trans-2,2'-dinitro-4-methylstilbene melting at 170° to 171° C. (recrystallized from benzene).

B. As in Example 2(C), a solution of 2 g. of trans-2,2'-dinitro-4-methylstilbene in 50 ml. of tetrahydrofuran was subjected to catalytic reduction using Raney nickel as a catalyst. The product was recrystallized from a mixture of benzene and petroleum benzin to give 1.4 g. (87.5% yield) of 2,2'-diamino-4-methyldibenzyl as colorless pillars melting at 78.5° to 79° C.

C. As in Example 2(D), a mixture of 6 g. of 2,2'-diamino-4-methyldibenzyl and 0.12 g. of anhydrous aluminum chloride was heated at 270° to 320° C. for 40 minutes and treated to give 4.48 g. (80.7% yield) of 3-methyliminodibenzyl. The product was distilled under reduced pressure, and the fraction boiling at 145° to 149° C./0.5 mmHg. was solidified and recrystallized from benzene to give pure crystals melting at 103.5° to 104° C. The amount of the complex of 2,2'-diamino-4-methyldibenzyl and aluminum chloride as recovered was 0.44 g.

EXAMPLE 20

To 3 g. of 2,2'-diamino-4-methyldibenzyl, 0.3 g. of the crude complex of 2,2'-diamino-4-methyldibenzyl with aluminum chloride as obtained in Example 19(C) was added, and the resultant mixture was heated at 290° to 320° C. for 1.5 hours and treated as in Example 2(D) to give 2.05 g. (74% yield) of 3-methyliminodibenzyl.

EXAMPLE 21

A mixture of 4 g. of 2,2'-diamino-4-methyldibenzyl and 0.15 g. of anhydrous stannic chloride was heated at 290° to 330° C. for 1.5 hours and treated as in Example 2(D) to give 2.54 g. (69% yield) of 3-methyliminodibenzyl.

EXAMPLE 22

A mixture of 4 g. of 2,2'-diamino-4-methyldibenzyl and 0.15 g. of titanium tetrachloride was heated at 290° to 330° C. for 2 hours and treated as in Example 2(D) to give 2.16 g. of 3-methyliminodibenzyl.

EXAMPLE 23

A mixture of 4 g. of 2,2'-diamino-4-methyldibenzyl and 0.12 g. of cupric chloride was heated at 290° to 320° C. for 2 hours and treated as in Example 2(D) to give 1.92 g. of 3-methyliminodibenzyl.

EXAMPLE 24

A mixture of 4 g. of 2,2'-diamino-4-methyldibenzyl and 0.3 g. of hexaaminecobalt chloride (luceo salt) was heated at 290° to 320° C. for 2 hours and treated as in Example 2(D) to give 2.23 g. of 3-methyliminodibenzyl.

EXAMPLE 25

A mixture of 3 g. of 2,2'-diamino-4-methyldibenzyl and 0.18 g. of phosphorus oxychloride was heated at 290° to 320° C. for 3 hours and treated as in Example 2(D) to give 1.2 g. of 3-methyliminodibenzyl.

EXAMPLE 26

A mixture of 3 g. of 2,2'-diamino-4-methyldibenzyl and 0.12 g. of iodine was heated at 300° to 330° C. for 2.5 hours as in Example 2(D) to give 1.38 g. of 3-methyliminodibenzyl.

EXAMPLE 27

A. In a solution of 1.2 g. of metallic sodium in 70 ml. of methanol, 13.5 g. of diethyl 2-nitro-4-chlorobenzyl phosphonate was dissolved. While stirring the solution at ambient temperature, a solution of 7 g. of 2-nitro-4-methylbenzaldehyde in 50 ml. of ethanol was dropwise added. After being stirred below 30° C. for 2 hours and allowed to stand overnight, the yellow crystals formed were filtered to give 9.8 g. (72.5% yield) of trans-2,2'-dinitro-4-chloro-4'-methylstilbene melting at 230° to 230.5° C. (recrystallized from benzene).

B. As in Example 2(C), 7 g. of trans-2,2'-dinitro-4-chloro-4'-methylstilbene was subjected to catalytic reduction. The product was recrystallized from isopropanol to give 4.5 g. (78.6% yield) of 2,2'-diamino-4-chloro-4'-methyldibenzyl as colorless needles melting at 83.5° to 84° C.

C. As in Example 2(D), a mixture of 4 g. of 2,2'-diamino-4-chloro-4'-methyldibenzyl and 0.1 g. of anhydrous aluminum chloride was heated at 330° to 350° C. for 1 hour and treated to give 2.6 g. (70% yield) of 3-chloro-7-methyliminodibenzyl. The product was distilled under reduced pressure, and the fraction boiling at 158° to 165° C./0.5 mmHg was solidified and recrystallized from a mixture of benzene and petroleum benzene to give crystals melting at 130° to 131° C.

The invention thus being described, it will be obvious that the same may be varied in many ways. Such variations are not to be regarded as a departure from the spirit and scope of the invention, and all such modifications as would be obvious to one skilled in the art are intended to be included herein.

What is claimed is:

1. A process for preparing asymmetric iminodibenzyl derivatives, which comprises condensing a 2-nitrobenzyl phosphonic ester of the formula:

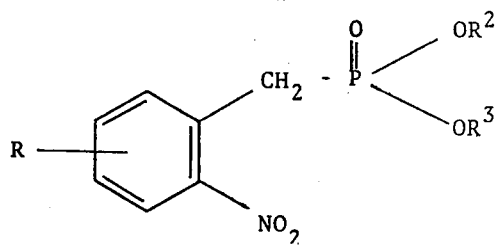

wherein R is one or more substituents selected from the group consisting of hydrogen, halogen, amino, sulfamoyl, lower alkyl, lower alkoxy and lower alkanoyl, and $R^2$ and $R^3$ are each hydrogen, lower alkyl, phenyl or phenyl (lower) alkyl, provided that when one of $R^2$ and $R^3$ is hydrogen, the other is different from hydrogen, with a 2-nitrobenzaldehyde of the formula:

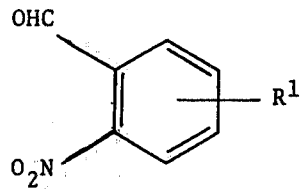

wherein $R^1$ is one or more substituents selected from the group consisting of hydrogen, halogen, amino, sulfamoyl, lower alkyl, lower alkoxy and lower alkanoyl, R and $R^1$ being asymmetrically attached to the respective positions of the benzene rings when R and $R^1$ are the same or different or being different when R and $R^1$ are attached to the same positions on the respective benzene rings, in an inert organic solvent in the presence of a condensing agent selected from the group consisting of an alkali metal alcoholate, sodium hydride and sodium amide, reducing the resultant 2,2'-dinitrostilbene of the formula:

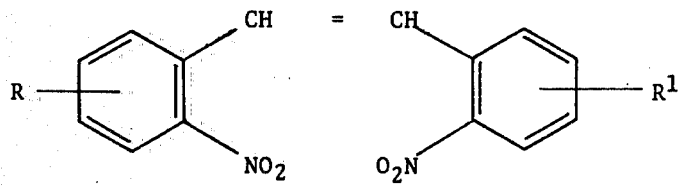

wherein R and $R^1$ are each the same as defined above, by catalytic hydrogenation or in the presence of a reducing agent, and ringclosing the resultant 2,2'-diaminodibenzyl of the formula:

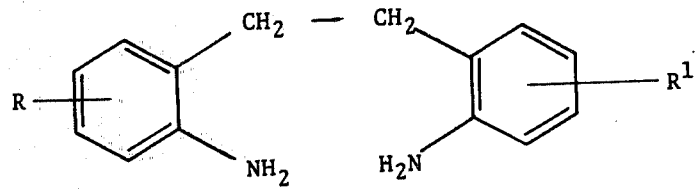

wherein R and $R^1$ are each the same as defined above, by heating in the presence or absence of a catalyst, to give an iminodibenzyl of the formula:

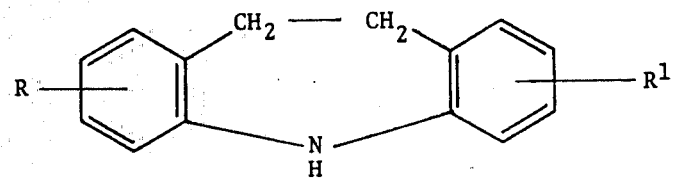

wherein R and $R^1$ are each the same as defined above.

2. The process according to claim 1, wherein the reduction is effected in a single step by reducing the 2,2'-dinitrostilbene with hydrogen in the presence of a catalyst selected from the group consisting of Raney nickel, platinum oxide and palladium on a carrier, or by treatment with metallic sodium and amyl alcohol.

3. The process according to claim 1, wherein the reduction is effected in two steps by first treating said 2,2'-dinitrostilbene with a reducing agent and then reducing the resultant 2,2'-diaminostilbene by catalytic hydrogenation or by treatment with metallic sodium and amyl alcohol.

4. The process according to claim 3, wherein the reducing agent employed in the first step is stannous chloride, iron and hydrochloric acid or zinc and hydrochloric acid.

5. The process according to claim 1, wherein the ring-closure is carried out by heating at a temperature of about 200°C. to 400°C.

6. The process according to claim 1, wherein the ring-closure is carried out by heating when the 2,2'-diaminodibenzyl compound is in the form of a salt, by heating in the presence of a catalyst selected from the group consisting of metallic salts, ammonium salts, phosphorus halides, phosphorus oxyhalides, complex compounds thereof with 2,2'-diaminodibenzyls, hydrohalides of 2,2'-diaminodibenzyls, iodine and ammonium complexes of metals when the 2,2'-diaminodibenzyl compound is in the free form or by heating in the presence of the 2,2'-diaminodibenzyl compound in the salt form or polyphosphoric acid when the 2,2'-diaminodibenzyl compound is in the free form.

7. The process according to claim 6, wherein said heating is carried out at a temperature of about 200°C. to 400°C.

8. The process according to claim 1, wherein the reduction is carried out first by treating with a reducing agent which is capable of converting a nitro group into an amino group and then by treating with a reducing agent which is capable of converting a double bond into a single bond.

* * * * *